US012383551B2

(12) United States Patent
Brewer et al.

(10) Patent No.: US 12,383,551 B2
(45) Date of Patent: *Aug. 12, 2025

(54) METHODS AND COMPOSITIONS FOR MAINTAINING OPIOID EFFICACY IN THE TREATMENT OF PAIN

(71) Applicant: East Carolina University, Greenville, NC (US)

(72) Inventors: Kori Brewer, Greenville, NC (US); Stefan Clemens, Greenville, NC (US)

(73) Assignee: East Carolina University, Greenville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/443,447

(22) Filed: Feb. 16, 2024

(65) Prior Publication Data

US 2024/0189301 A1 Jun. 13, 2024

Related U.S. Application Data

(63) Continuation of application No. 17/556,132, filed on Dec. 20, 2021, now Pat. No. 11,925,635, which is a continuation of application No. 16/758,584, filed as application No. PCT/US2018/057449 on Oct. 25, 2018, now Pat. No. 11,202,777.

(60) Provisional application No. 62/577,443, filed on Oct. 26, 2017.

(51) Int. Cl.
*A61K 31/485* (2006.01)
*A61K 31/428* (2006.01)
*A61P 25/04* (2006.01)
*A61K 45/06* (2006.01)

(52) U.S. Cl.
CPC .......... *A61K 31/485* (2013.01); *A61K 31/428* (2013.01); *A61P 25/04* (2018.01); *A61K 45/06* (2013.01)

(58) Field of Classification Search
CPC ...... A61K 31/485; A61K 31/428; A61P 25/04
USPC ................................. 514/282, 367
See application file for complete search history.

(56) References Cited

U.S. PATENT DOCUMENTS

| 11,202,777 B2* | 12/2021 | Brewer | A61K 31/428 |
| 2013/0165468 A1 | 6/2013 | Aung-Din et al. | A61K 31/485 514/282 |
| 2015/0352099 A1 | 12/2015 | Braithwaite et al. | A61K 31/485 514/282 |

FOREIGN PATENT DOCUMENTS

WO 2017/031338 2/2017

OTHER PUBLICATIONS

Harris et al., "Involvement of D2 dopamine receptors in the nucleus accumbens in the opiate withdrawal syndrome," Letters to Nature, vol. 371, No. 6493, Sep. 8, 1994, pp. 155-157.
Brewer et al., "Dopamine D3 receptor dysfunction prevents antinociceptive effects of morphine in the spinal cord," Frontiers in Neural Circuits, vol. 8, Article 62, Jun. 11, 2014, pp. 1-10.
Comella, Cynthia L., "Treatment of Restless Legs Syndrome," Neurotherapeutics, vol. 11, 2014, pp. 177-187.
Yeung et al., "Sleep Attacks in Patients with Parkinson's Disease on Dopaminergic Medications: A Systematic Review," International Parkinson and Movement Disorder Society, 2014, pp. 307-316.
Lipford et al., "Long-term use of pramipexole in the management of restless legs syndrome," Sleep Med, Dec. 13, 2012.
Harris et al., "Involvement of D2 dopamine receptors in the nucleus accumbens in the opiate withdrawal syndrome," Letters to Nature, vol. 371, No. 6493, pp. 155-157.
Zhu et al., "Therapeutic target database 2020: enriched resource for facilitating research and early development of targeted therapeutics," Nucleic Acids Research, Jan. 1, 2020, 6 pages.
Makhinson et al., "A successful Treatment of Buprenorphine Withdrawal with the Dopamine Receptor Agonist Pramipexole," The American Journal on Addictions, 23, 2014, pp. 475-477.
International Preliminary Report on Patentability corresponding to International Application No. PCT/US2018/057449 mailed May 7, 2020.
Cook et al. "Selective attenuation of the antinociceptive effects of u opioids by the putative dopamine D3 agonist 7-OH-DPAT", Psychopharmacology 144:239-247 (1999).
International Search Report and Written Opinion corresponding to International Application No. PCT/US2018/057449 mailed Feb. 21, 2019.
Li et al. "Role of dopamine D3 receptors in basal nociception regulation and in morphine-induced tolerance and withdrawal", Brain Research 1443:80-84 (2012).
Charles D. Cook, et al.: "Selective attenuation of the antinociceptive effects of u opioids by the putative dopamine D3 agonist 7-OH-DPAT." Psychopharmacology vol. 144, Jan. 1, 1999, pp. 239 247, Original Investigation.
Harris, et al.: "Involvement of D2 dopamine receptors in the nucleus accumbens in the opiate withdrawal syndrome", Nature, vol. 371, No. 6493, Sep. 1, 1994, pp. 155-157, XP055817743; Division of Behavioral Neurobiology, Department of Mental Health Sciences.
Zhu Feng et al: "Therapeutic Target Database—R-N-Propylnorapomorphine", Therapeutic Target Database, Jan. 1, 2020, XP055817750.
Michael Makhinson, et al: "A successful Treatment of Buprenorphine Withdrawal with the Dopamine Receptor Agonist Pramipexole: Treatment of Buprenorphine Withdrawal with Pramipexole", The American Journal on Addictions, vol. 23, No. 5, Sep. 1, 2014, pp. 475 477, 2014 Copyright American Academy of Addiction Psychiatry.

(Continued)

*Primary Examiner* — Charanjit Aulakh
(74) *Attorney, Agent, or Firm* — Stanek Lemon Crouse & Lemon, PA

(57) ABSTRACT

The present invention provides methods for treating and/or managing pain. The invention further provides methods for reducing or inhibiting opioid tolerance, reducing risk of opioid addiction or dependence, restoring opioid efficacy, and enhancing the therapeutic effect of an opioid. The invention further provides compositions for use in the methods of the invention.

13 Claims, 4 Drawing Sheets

(56) References Cited

OTHER PUBLICATIONS

Tao Li et al: "Role of dopamine D3 receptors in basal nociception regulation and in morphine-induces tolerance and withdrawal", Brain Research, Elsevier, Amsterdam, NL, vol. 1433, Nov. 19, 2011, pp. 80-84, ScienceDirect.

Pritchard et al: "7-OH-DPAT and PD 128907 Selectively Activate the D3 Dopamine Receptor in a Novel Environment", Neuropsychopharmacology (2003) 28, 100 107; 2003 Nature Publishing Group www.neuropsychopharmacology.org.

* cited by examiner

METHODS AND COMPOSITIONS FOR MAINTAINING OPIOID EFFICACY IN THE TREATMENT OF PAIN

STATEMENT OF PRIORITY

The present application is a continuation of U.S. application Ser. No. 17/556,132, filed Dec. 20, 2021, which is a continuation of U.S. application Ser. No. 16/758,584, filed Apr. 23, 2020 (now U.S. Pat. No. 11,202,777), which is a 35 U.S.C. § 371 national phase application of PCT International Application No. PCT/US2018/057449, having an international filing date of Oct. 25, 2018, which claims the benefit, under 35 USC § 119(e), of U.S. Provisional Application No. 62/577,443, filed Oct. 26, 2017, the entire contents of which are hereby incorporated herein by reference in their entireties.

RESERVATION OF COPYRIGHT

A portion of the disclosure of this patent document contains material which is subject to copyright protection. The copyright owner, East Carolina University, Greenville, North Carolina, a constituent institution of the University of North Carolina, has no objection to the reproduction by anyone of the patent document or the patent disclosure, as it appears in U.S. Patent and Trademark Office patent files or records, but otherwise reserves all copyright rights whatsoever.

FIELD OF THE INVENTION

The present invention is directed to methods and compositions for maintaining opioid efficacy in the treatment and management of pain.

BACKGROUND OF THE INVENTION

Chronic pain is a major health risk factor, with a prevalence of ~10% in the general population. Current cost estimates of treatment/loss of productivity exceed $600B/year. The current treatment options target inhibitory mu-opioid receptors (MORs). While initially highly beneficial, these drugs lose their efficacy over time and patients develop drug tolerance and the risk for addiction. The mechanisms that underlie this switch are partially identified and involve signaling cascades that modulate the efficacy of the MOR. Solving the problem of opioid tolerance remains one of the last remaining hurdles in developing an effective long-term treatment for chronic pain.

The present invention overcomes previous shortcomings in the art by providing methods and compositions for maintaining opioid efficacy in the treatment and management of chronic pain.

SUMMARY OF THE INVENTION

In one aspect, the present invention provides a method of treating pain in a subject in need thereof, comprising administering to the subject an effective amount of an opioid and a dopamine type 3 receptor (D3R) agonist, thereby treating pain in the subject.

In a further aspect, the present invention provides a method of reducing or inhibiting opioid tolerance in a subject in need thereof, comprising administering to the subject an effective amount of an opioid and a dopamine type 3 receptor (D3R) agonist, thereby reducing or inhibiting opioid tolerance in the subject.

In an additional embodiment, the present invention provides a method of reducing risk of opioid addiction and/or dependence in a subject in need thereof, comprising administering to the subject an effective amount of an opioid and a dopamine type 3 receptor (D3R) agonist, thereby reducing risk of opioid addiction or dependence in the subject.

Also provided herein is a method of restoring opioid efficacy in a subject in need thereof, comprising administering to the subject an effective amount of an opioid and a dopamine type 3 receptor (D3R) agonist, thereby restoring opioid efficacy in the subject.

Also provided herein is a method for enhancing the therapeutic effect of an opioid in a subject, comprising: a) administering an effective amount of a D3R agonist to a subject; and b) administering a subtherapeutic amount of the opioid to the subject, wherein the therapeutic effect of the subtherapeutic amount of the opioid is enhanced as compared to the effect of the subtherapeutic amount of the opioid administered without the D3R agonist.

In another aspect, the present invention provides a composition comprising: (a) at least one opioid; (b) at least one dopamine type 3 receptor (D3R) agonist; and (c) a pharmaceutically acceptable carrier, excipient or diluent.

In an additional embodiment, the present invention provides a kit for treating pain, comprising at least one opioid and at least one dopamine type 3 receptor agonist.

The foregoing and other objects and aspects of the present invention are explained in greater detail in reference to the drawings and description set forth herein.

DETAILED DESCRIPTION OF THE INVENTION

Figure 1:
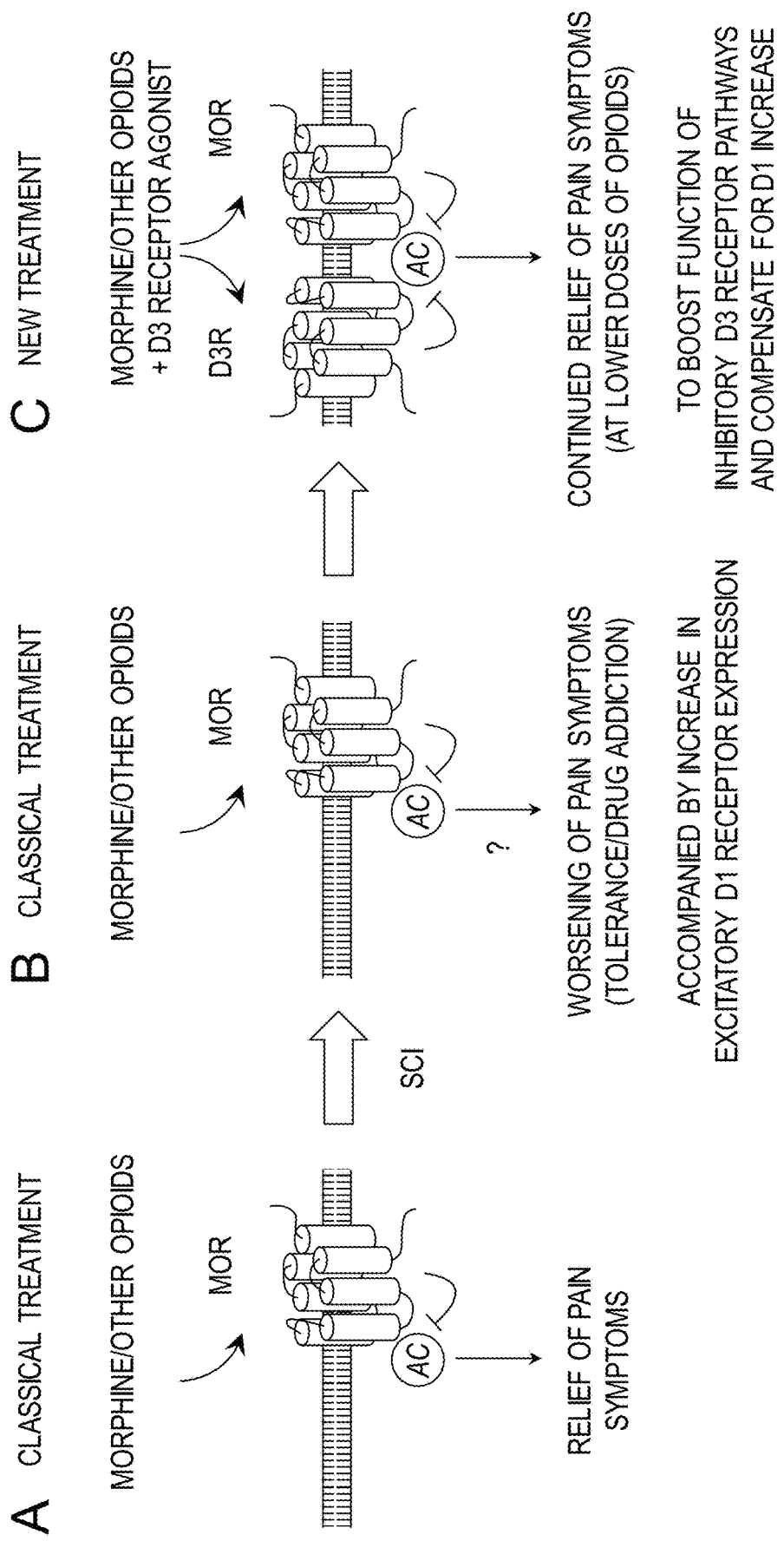
FIG. 1: Model of changing receptor interactions in the treatment of chronic pain. Panel A. Acute treatment with morphine or another opioid targets predominantly the u-opioid receptor (MOR), thereby starting an intracellular signaling cascade that results in the relief of the pain symptoms. Under normal conditions, activation of MOR leads to decreased cAMP and reduction in cellular activity (i.e., reduced pain). Panel B. Over time, this signaling cascade loses its efficacy, and treatment doses have to be increased to maintain a symptomatic effect. This then leads to drug tolerance and can contribute to drug addiction. Spinal cord injury upregulates endogenous opioids, leading to desensitization of MOR and loss of opioid effect. D1R is also upregulated, inducing GRK-mediated MOR internalization and reducing MOR responsiveness. Panel C. A combination therapy of morphine+a dopamine D3 receptor agonist (D3R) will provide continued relief in the long-term treatment of chronic pain (and thus prevent opioid tolerance and drug addiction). Concomitant activation of D3Rs and MORs will restore MOR action in injured conditions.
Figure 2:
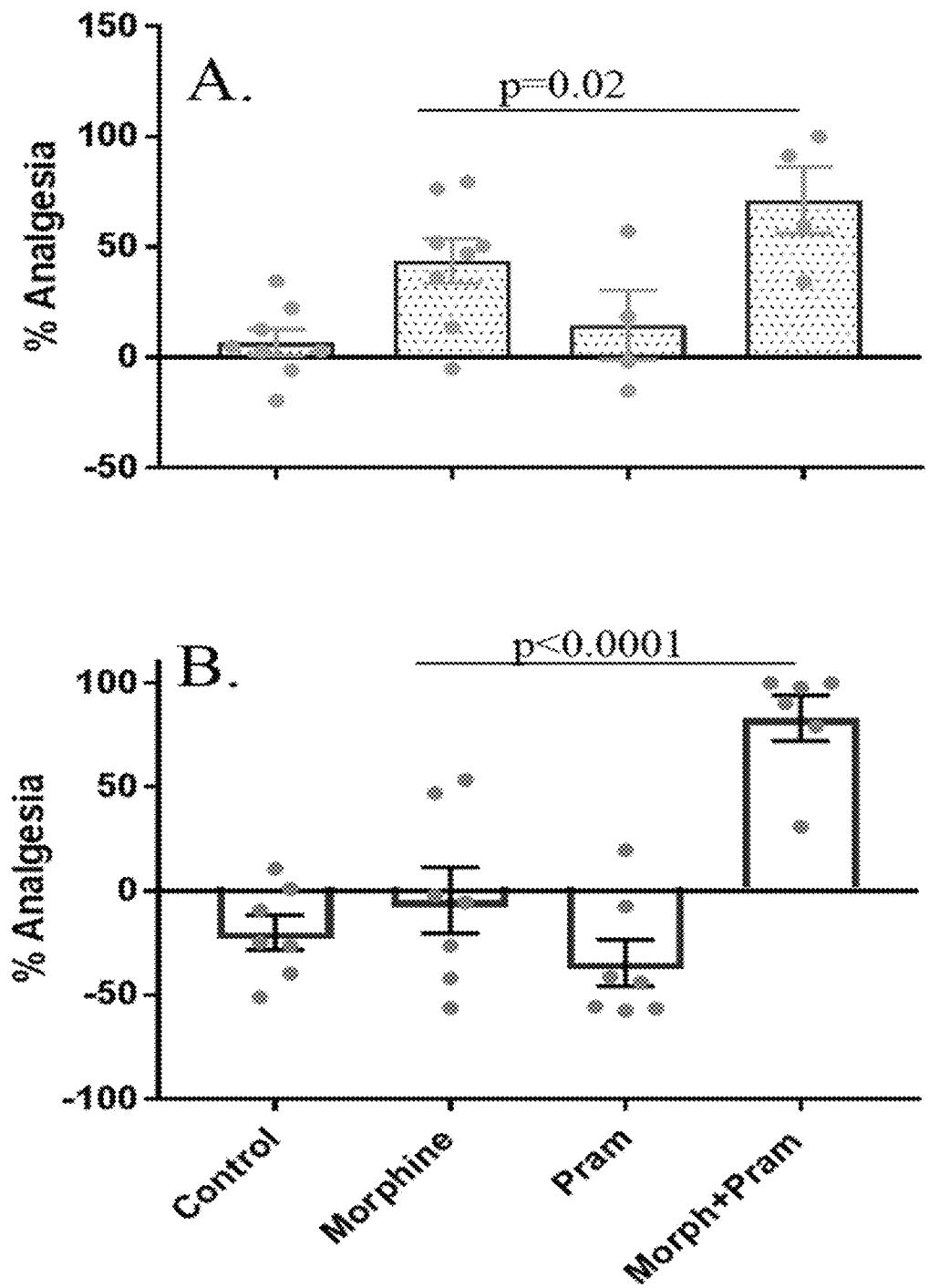
FIG. 2: Proof-of-concept that morphine co-treatment with a D3R agonist improves drug responsiveness in normal animals and animals with chronic pain. Panel (A). In healthy control animals, acute morphine treatment improves analgesia significantly, while treatment with the D3 receptor agonist, pramipexole (PRAM) does not. Adjuvant treatment of both morphine and PRAM significantly increases the analgesic effect over morphine alone. Panel (B). In animals with spinal cord injury (SCI), neither morphine nor PRAM have any analgesic effect, however adjuvant treatment application significantly and strongly restores analgesia.
Figure 3:
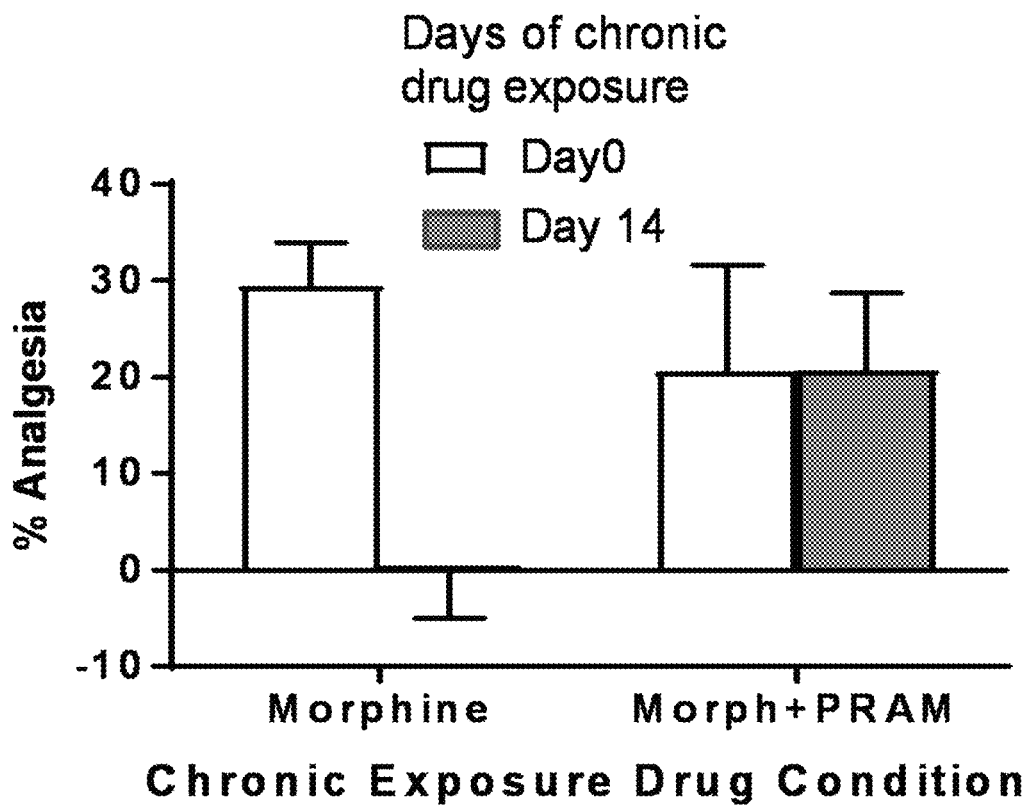
FIG. 3: Long-term application of morphine leads to a complete loss of analgesic effect after 2 weeks (left pair of bars, while adjuvant treatment of the D3 agonist PRAM with morphine maintains the opioid's efficacy on analgesia.
Figure 4:
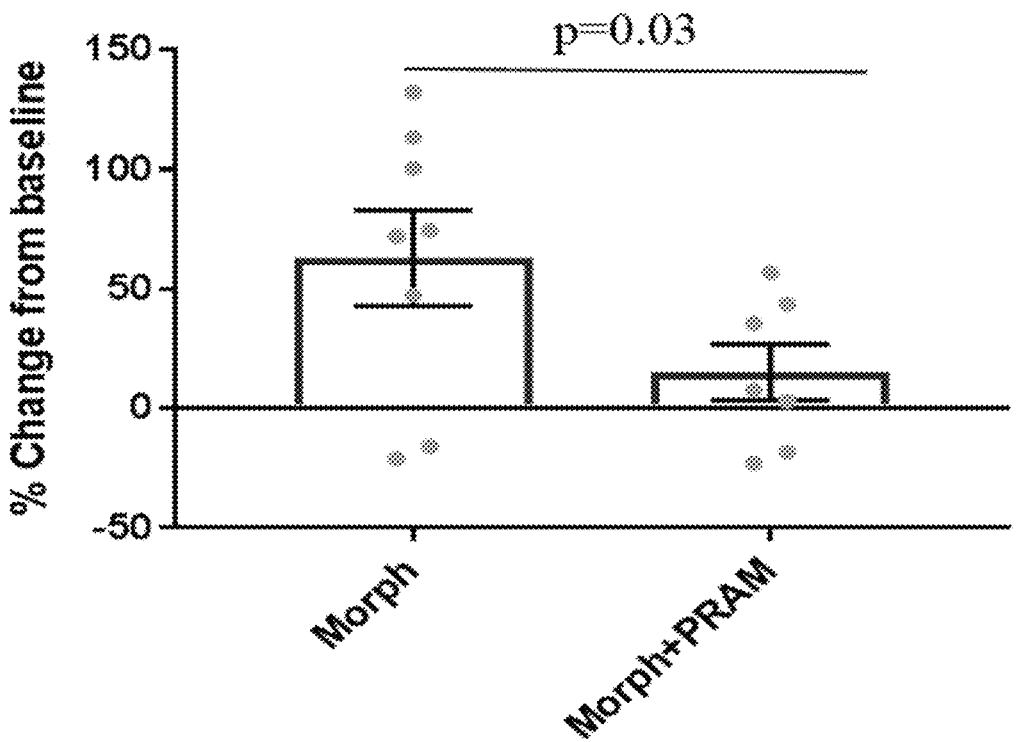
FIG. 4: Morphine treatment induces preference for the drug-paired chamber (left bar), and this preference was significantly decreased with the combination of morphine with the D3 receptor compound PRAM did not (right bar).
Figure 5:
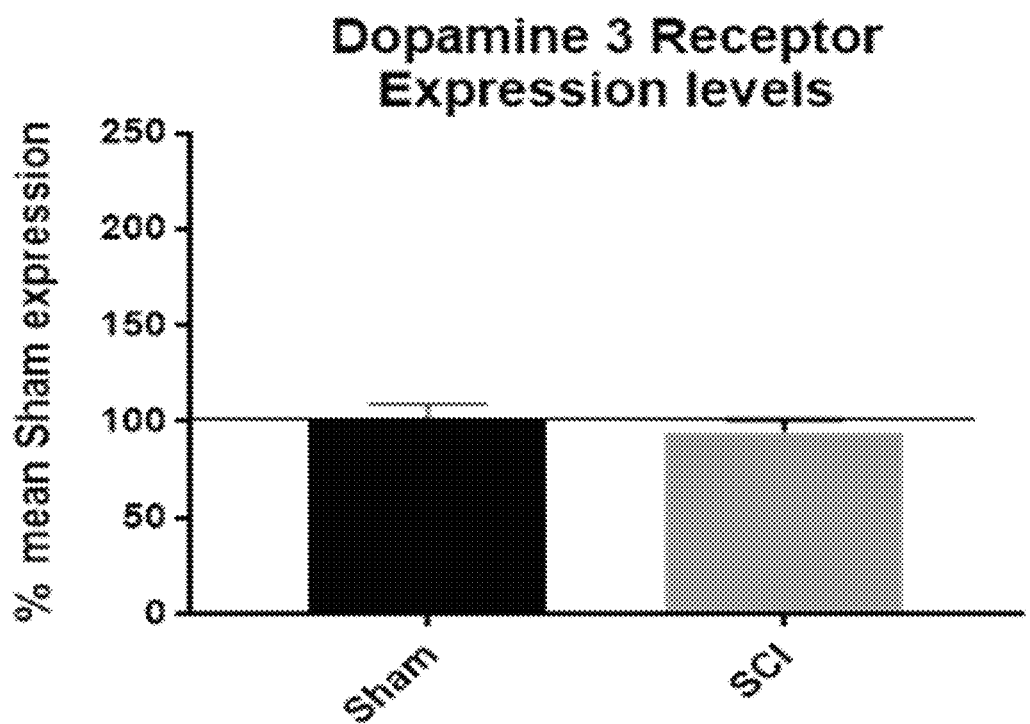
FIG. 5: In SCI animals, D3R protein expression is unchanged.
Figure 6:
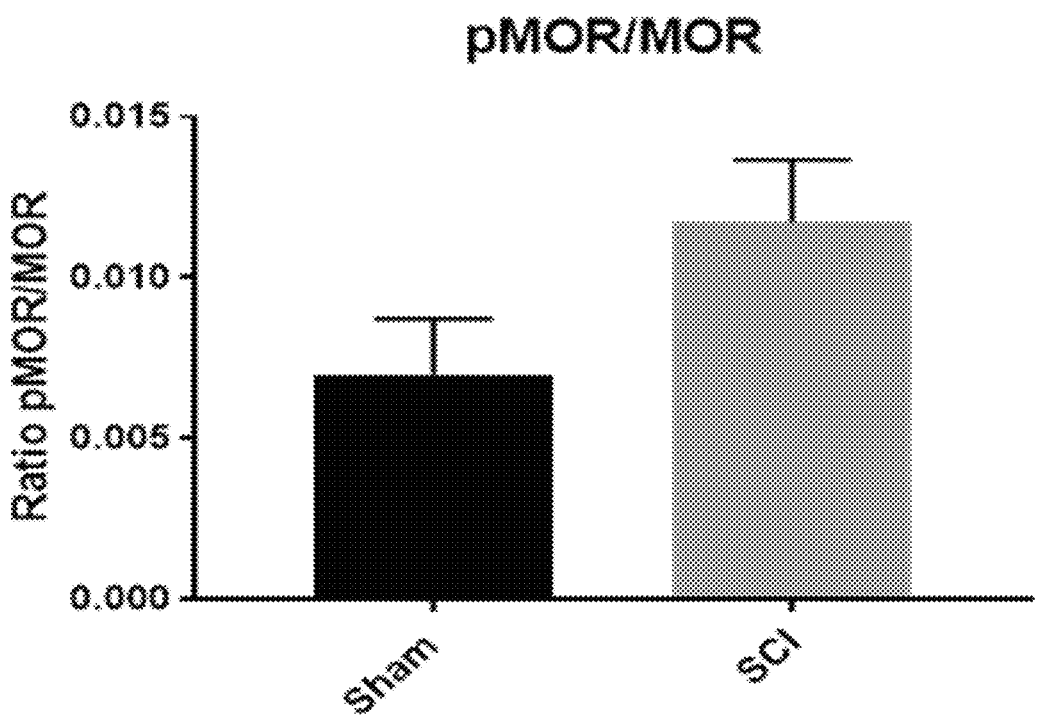
FIG. 6: In SCI animals, the ratio of pMOR/total MOR protein expression is increased versus sham animals.

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

The present invention is based on the unexpected discovery that the administration of a dopamine 3 receptor agonist in combination with an opioid to a subject in need thereof has the effect of maintaining and/or enhancing the efficacy of the opioid and/or reducing the risk of dependence and/or addiction and/or accidental overdose and/or allows for a lower dose of opioid to be administered than the dose a subject previously required to achieve pain relief.

Thus, in one embodiment, the present invention provides a method of treating pain in a subject in need thereof, comprising administering to the subject an effective amount of an opioid and a dopamine type 3 receptor (D3R) agonist, thereby treating pain in the subject.

In another embodiment, the present invention provides a method of reducing or inhibiting opioid tolerance in a subject in need thereof, comprising administering to the subject an effective amount of an opioid and a dopamine type 3 receptor (D3R) agonist, thereby reducing or inhibiting opioid tolerance in the subject.

In an additional embodiment, the present invention provides a method of reducing risk of opioid addiction and/or dependence in a subject in need thereof, comprising administering to the subject an effective amount of an opioid and a dopamine type 3 receptor (D3R) agonist, thereby reducing risk of opioid addiction and/or dependence in the subject.

Also provided herein is a method of restoring opioid efficacy in a subject in need thereof, comprising administering to the subject an effective amount of an opioid and a dopamine type 3 receptor (D3R) agonist, thereby restoring opioid efficacy.

In each of the methods of the invention, the effect of the combination treatment, e.g., change in the level of pain, tolerance, risk of addition or dependence, or efficacy can be quantitated by methods that are well known in the art and as described herein.

In the methods of this invention, the opioid and the D3R agonist can be administered in the same composition or formulation and/or in separate compositions or formulations. Said separate compositions and/or formulations can be administered simultaneously, concurrently and/or in any order and/or in any interval of minutes, days, weeks, etc. In some embodiments, the D3R agonist may be administered about 1, 2, 3, 4, 5, 10, 15, 20, 25, 30, 35, 40, 45, 50, or 55 minutes or 1, 2, 3, 4, 5, 6, 12, or 18 hours or 1, 2, 3, 4, 5, 6, or 7 or more days before or after administration of the opioid. One or more doses of the D3R against may be administered before or after one or more doses of the opioid.

Nonlimiting examples of the type of pain that can be treated according to a method of this invention include acute pain, such as post-surgical pain, pain from trauma (e.g., acute musculoskeletal injury, etc.), renal colic pain, sickle cell crisis pain, pain associated with childbirth, abdominal pain associated with acute illness, burn injury, etc. Additional nonlimiting examples include chronic pain, such as cancer pain, and chronic non-malignant pain (CNMP), including for example, back pain, joint pain, arthritis pain, migraine pain, cluster headache pain, nerve injury pain, dental pain, neuropathic pain, fibromyalgia pain, diabetic neuropathy pain, chronic inflammatory pain, allodynia, hyperalgesia, pain from shingles, etc. Pain can be mechanical sensitivity, thermal sensitivity, or other types of pain.

Nonlimiting examples of an opioid that can be administered according to a method of this invention include generic opioid drugs (e.g., morphine sulfate, fentanyl, methadone hydrochloride, oxymorphone hydrochloride); brand name opioid drugs (e.g., Abstral (fentanyl), Actiq (fentanyl), Avinza (morphine sulfate extended-release capsules), Butrans (buprenorphine transdermal system), Demerol (meperidine [also known as isonipecaine or pethidine]), Dilaudid (hydromorphone [also known as dihydromorphinone]), Dolophine (methadone hydrochloride tablets), Duragesic (fentanyl transdermal system), Fentora (fentanyl), Hysingla (hydrocodone), Methadosc (methadone), Morphabond (morphinc), Nucynta ER (tapentadol extended-release oral tablets), Onsolis (fentanyl), Oramorph (morphine), Oxaydo (oxycodone), Roxanol-T (morphinc), Sublimaze (fentanyl), Xtampza ER (oxycodonc), Zohydro ER (hydrocodonc)); and combination formulations of opioid drugs (e.g., Anexsia (hydrocodone containing acetaminophen), Co-Gesic (hydrocodone containing acetaminophen), Embeda (morphine sulfate and naltrexone extended-release capsules), Exalgo (hydromorphone hydrochloride extended-release tablets), Hycet (hydrocodone containing acetaminophen), Hycodan (hydrocodone containing homatropinc), Hydromet (hydrocodone containing homatropinc), Ibudonc (hydrocodone containing ibuprofen), Kadian (morphine sulfate extended-release tablets), Liquicet (hydrocodone containing acetaminophen), Lorcet (hydrocodone containing acetaminophen), Lorcet Plus (hydrocodone containing acetaminophen), Lortab (hydrocodone containing acetaminophen), Maxidone (hydrocodone containing acetaminophen), MS Contin (morphine sulfate controlled-release tablets), Norco (hydrocodone containing acetaminophen), Opana ER (oxymorphone hydrochloride extended-release tablets), OxyContin (oxycodone hydrochloride controlled-release tablets), Oxycet (oxycodone containing acetaminophen), Palladone (hydromorphone hydrochloride extended-release capsules), Percocet (oxycodone containing acetaminophen), Percodan (oxycodone containing aspirin), Reprexain (hydrocodone containing ibuprofen), Rezira (hydrocodone containing pseudoephedrine), Roxicet (oxycodone containing acetaminophen), Targiniq ER (oxycodone containing naloxone), TussiCaps (hydrocodone containing chlorpheniramine), Tussionex (hydrocodone containing chlorpheniramine), Tuzistra XR (codeine containing chlorpheniraminc), Tylenol #3 and #4 (codeine containing acetaminophen), Vicodin (hydrocodone containing acetaminophen), Vicodin ES (hydrocodone containing acetaminophen), Vicodin HP (hydrocodone containing acetaminophen), Vicoprofen (hydrocodone containing ibuprofen), Vituz (hydrocodone containing chlorpheniramine), Xartemis XR (oxycodone containing acetaminophen), Xodol (hydrocodone containing acetaminophen), Zolvit (hydrocodone containing acetaminophen), Zutripro (hydrocodone containing chlorpheniramine and pseudoephedrine), Zydone (hydrocodone containing acetaminophen)). The opioids of this invention can be employed in the methods of this invention singly or in any combination and/or ratio.

D3R agonists can be any molecule that activates the D3R. In some embodiments, the agonist may specifically activate D3R. In some embodiments, the agonist may predominantly activate D3R over other dopamine receptors. Nonlimiting examples of a dopamine 3 receptor agonist of this invention include enafadotride, cabergoline, PD 128907, pramipexole (Mirapex), pergolide, and rotigotine (Neupro™), singly or in any combination and/or ratio.

It is contemplated that subjects to whom the methods of this invention are applied can receive a lower dose of an opioid when it is administered in combination with a D3R agonist of this invention. By "lower dose" is meant a reduced amount of an opioid relative to the amount that the subject is taking or has been taking without a D3R agonist in combination (e.g., at least about 5%, 10%, 15%, 20%, 25%, 30%, 35%, 40%, 45%, or 50% less). This is because the D3R agonist enhances the efficacy of the opioid, resulting in the same or a better level of pain relief and/or pain control in the subject relative to the amount of pain relief and/or pain control the subject is experiencing in the absence of the D3R agonist.

Thus, in one embodiment, the present invention provides a method for enhancing the therapeutic effect of an opioid in a subject, comprising: a) administering an effective amount of a D3R agonist to a subject; and b) administering a subtherapeutic amount of the opioid to the subject, wherein the therapeutic effect of the subtherapeutic amount of the opioid is enhanced as compared to the effect of the subtherapeutic amount of the opioid administered without the D3R agonist. A "subtherapeutic" amount is an amount of the opioid that does not provide any therapeutic effect when administered on its own, i.e., below the standard dose range for treating acute pain or the standard dose range for treating chronic pain. In some embodiments, a "subtherapeutic amount" is an amount that is less than the amount the subject has been taking to achieve pain reduction and/or pain control in the absence of a D3R agonist (e.g., for chronic pain).

In some embodiments of this invention, a dopamine 1 receptor (DIR) antagonist can be administered in the methods described herein and/or included in the compositions described herein.

In some embodiments, the methods of this invention are carried out without the inclusion of a D1R antagonist and in some embodiments, the compositions do not comprise or include a D1R antagonist. For example, in some embodiments, a composition of this invention can comprise (a) at least one opioid; (b) at least one dopamine type 3 receptor agonist; and (c) a pharmaceutically acceptable carrier, excipient or diluent, with the proviso that the composition does not comprise a D1R antagonist. As another example, in some embodiments, the present invention provides a method of treating pain in a subject in need thereof, comprising administering to the subject an effective amount of an opioid and a dopamine type 3 receptor (D3R) agonist, with the proviso that a D1R antagonist is not administered to the subject.

Nonlimiting examples of a D1R antagonist include ecopipam (SCH 39166), SCH 23390, SKF 83566, singly or in any combination and/or ratio.

It is contemplated that any specific opioid, D3R agonist and/or D1R antagonist, singly or in any combination, can be excluded from the methods and/or compositions of this invention.

In further embodiments, the present invention additionally provides compositions that can be employed in the methods of this invention. Thus, in one embodiment, the present invention provides a composition comprising: (a) at least one opioid; (b) at least one D3 receptor agonist; and (c) a pharmaceutically acceptable carrier, excipient or diluent. The composition can be a pharmaceutical composition or formulation that can comprise additional therapeutic agents or techniques. See, e.g., Remington, *The Science And Practice of Pharmacy* (latest edition). agents for the treatment and/or management of chronic pain and/or acute pain.

Nonlimiting examples of an additional agent that can be included in a pharmaceutical composition or formulation and/or can be administered according to the methods of this invention include analgesic agents, non-steroid anti-inflammatory (NSAID) agents (e.g., Ibuprofen, Naproxen, Ketoprofen, Diclofenac, Fenoprofen, Ketoroloac, Meloxicam, Indomethacin, Piroxicam, Cox-2 inhibitors, etc.), salicylates (e.g., aspirin, magnesium salicylate, diflunisal, etc.), acetaminophen, codeine, chlorpheniramine, pseudoephedrine, homatropine, triptans, and ergots, in any combination and/or ratio.

In terms of administration of a composition of this invention, the most suitable route in any given case will depend on the nature and severity of the condition and/or the pharmaceutical formulation being administered. The active agents described herein can be formulated for administration in a pharmaceutical carrier in accordance with known practices.

The compositions of the present invention may be suitable for and formulated for parenteral, oral, inhalation spray, topical (i.e., both skin and mucosal surfaces, including airway surfaces), rectal, nasal, buccal (e.g., sub-lingual), vaginal or implanted reservoir administration, etc. where the most suitable route in any given case will depend on the nature and severity of the condition being treated in combination with the drug profile of the compound described herein as would be understood by one of ordinary skill in the art.

For topical administration, suitable forms include, but are not limited to an ointment, cream, emulsion, microemulsion, a gel, a dispersion, a suspension, a foam, an aerosol, a liquid, a droplet, and suitable transdermal delivery systems known in the art, such as patches and bandages, dressing, gauze and the like including the medicament described herein. Topical administration may further include articles of clothing such as socks or hosiery including the medicament described herein.

The term "parenteral" as used herein includes subcutaneous, intradermal, intravenous, intramuscular, intraperitoneal, intra-articular, intra-synovial, intrasternal, intrathecal, intra-hepatic, intralesional and intracranial injection or infusion techniques.

Compositions for injection will include the active ingredient together with suitable carriers including propylene glycol-alcohol-water, isotonic water, sterile water for injection (USP), EmulPhor™-alcohol-water, Ccremophor-EL™, polyvinyl pyrrolidone, lecithin, arachis oil or sesame oil, with other additives for aiding solubility or preservation may also be included, or other suitable carriers known to those skilled in the art. Accordingly, these carriers may be used alone or in combination with other conventional solubilizing agents such as ethanol, propylene glycol, or other agents known to those skilled in the art.

Compositions for oral administration may be, for example, solid preparations such as tablets, sugar-coated tablets, hard capsules, soft capsules, granules, powders, gelatins, and the like, with suitable carriers and additives being starches, sugars, binders, diluents, granulating agents, lubricants, disintegrating agents and the like. Because of their case of use and higher patient compliance, tablets and capsules represent the most advantageous oral dosage forms for many medical conditions.

Similarly, compositions for liquid preparations include solutions, emulsions, dispersions, suspensions, syrups, elixirs, and the like with suitable carriers and additives being water, alcohols, oils, glycols, preservatives, flavoring agents, coloring agents, suspending agents, and the like.

Where the compounds described herein are to be applied in the form of solutions or injections, the compounds may be used by dissolving or suspending in any conventional diluent. The diluents may include, for example, physiological saline, Ringer's solution, an aqueous glucose solution, an aqueous dextrose solution, an alcohol, a fatty acid ester, glycerol, a glycol, an oil derived from plant or animal sources, a paraffin and the like. These preparations may be prepared according to any conventional method known to those skilled in the art.

Compositions for nasal administration may be formulated as aerosols, drops, powders and gels. Aerosol formulations typically comprise a solution or fine suspension of the active ingredient in a physiologically acceptable aqueous or non-aqueous solvent. Such formulations are typically presented in single or multidose quantities in a sterile form in a sealed container. The sealed container can be a cartridge or refill for use with an atomizing device. Alternatively, the sealed container may be a unitary dispensing device such as a single use nasal inhaler, pump atomizer or an aerosol dispenser fitted with a metering valve set to deliver a therapeutically effective amount, which is intended for disposal once the contents have been completely used. When the dosage form comprises an aerosol dispenser, it will contain a propellant such as a compressed gas, air as an example, or an organic propellant including a fluorochlorohydrocarbon or fluorohydrocarbon.

Compositions suitable for buccal or sublingual administration include tablets, lozenges, gelatins, and pastilles, wherein the active ingredient is formulated with a carrier such as sugar and acacia, tragacanth or gelatin and glycerin.

In particular embodiments, the present invention provides a pharmaceutical formulation including the compound described herein wherein the pharmaceutical formulation is a parenteral formulation. In some embodiments, the parenteral formulation is an intravenous formulation. In some embodiments the parenteral formulation is an intraperitoneal formulation. In other embodiments, the present invention provides a pharmaceutical formulation including the compound described herein wherein the pharmaceutical formulation is an oral formulation.

According to the present invention, methods of this invention include administering an effective amount of a composition of the present invention as described above to the subject. The effective amount of the composition, the use of which is in the scope of present invention, will vary somewhat from subject to subject, and will depend upon factors such as the age and condition of the subject and the route of delivery. Such dosages can be determined in accordance with routine pharmacological procedures known to those skilled in the art. A composition of the present invention can comprise the active agents in an amount ranging from a lower limit from about 0.01, 0.05, 0.10, 0.50, 1.0, 5.0, or 10% to an upper limit ranging from about 10, 20, 30, 40, 50, 60, 70, 80, 90, 95, 96, 97, 98, 99, or 100% by weight of the composition. In some embodiments, the active agents include from about 0.05 to about 95% by weight of the composition. In other embodiments, the active agents can include from about 0.05 to about 60% by weight of the composition. In still other embodiments, the active agents include from about 0.05 to about 10% by weight of the composition.

Embodiments of the present invention further provide kits comprising, consisting essentially of or consisting of one or more containers having pharmaceutical dosage units comprising an effective amount of at least one $D_1$ receptor antagonist, at least one $D_3$ receptor agonist and optionally an opioid agonist, wherein the container is packaged with optional instructions for the treatment of pain.

The effective dosage of any specific active agent will vary somewhat from composition to composition, patient to patient, and will depend upon the condition of the patient and the route of delivery. As a general proposition, a dosage from about 0.1 to about 50 mg/kg will have therapeutic efficacy, with still higher dosages potentially being employed for oral administration, wherein aerosol administration is usually lower than oral or intravenous administration. Toxicity concerns at the higher level may restrict intravenous dosages to a lower level such as up to about 10 mg/kg, all weights being calculated based upon the weight of the active base, including the cases where a salt is employed. For the opioid component, a typical dose may range from about 0.1 mg/day to about 6 mg/day for intravenous or intramuscular administration. A dosage from about 0.1 mg/day to about 60 mg/day may be employed for oral administration. The D3R agonist dose may range from about 0.05 mg/day to about 50 mg/day.

In particular embodiments, administration to a subject such as a human, a dosage of from about 0.1 mg/day (e.g., about 1.0 mg/day), up to about 60 mg/day for opioid and from about 0.05 mg/day to about 100 mg/day (e.g., about 50 mg/day) for D3R agonist or more can be employed. Depending on the solubility of the particular formulation of active agents administered, the dose, which in some embodiments, can be in hourly (e.g., every four hours; every six hours; every 12 hours, etc.), daily (e.g., once a day; twice a day, etc.), weekly (e.g., once a week; twice a week; four times a week, etc.), monthly and/or yearly increments, can be divided among one or several unit dose administrations.

Definitions

As used herein, "a" or "an" or "the" can mean one or more than one. Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of 20%, 10%, 5%, 1%, 0.5%, or even 0.1% of the specified amount.

The terms "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

The term "modulate," "modulates" or "modulation" refers to enhancement (e.g., an increase) or inhibition (e.g., a reduction) in the specified activity.

The term "management" as used herein refers to the ability to affect a method, process, state of being, disorder or the like. The effect may be that of prevention, treatment or modulation.

By the terms "treat," "treating" or "treatment of," it is intended that the severity of the disorder or the symptoms of the disorder are reduced, or the disorder is partially or entirely eliminated, as compared to that which would occur in the absence of treatment. Treatment does not require the achievement of a complete cure of the disorder.

By the terms "preventing" or "prevention," it is intended that the inventive methods eliminate or reduce the incidence or onset of the disorder, as compared to that which would occur in the absence of the measure taken. Alternatively stated, the present methods slow, delay, control, or decrease the likelihood or probability of the disorder in the subject, as compared to that which would occur in the absence of the measure taken.

A "therapeutically effective" or "effective" amount is intended to designate a dose that causes a relief of symptoms of a disease or disorder as noted through clinical testing and evaluation, patient observation, and/or the like. "Effective amount" or "effective" can further designate a dose that causes a detectable change in biological or chemical activity. The detectable changes may be detected and/or further quantified by one skilled in the art for the relevant mechanism or process. Moreover, "effective amount" or "effective" can designate an amount that maintains a desired physiological state, i.e., reduces or prevents significant decline and/or promotes improvement in the condition of interest. As is generally understood in the art, the dosage will vary depending on the administration routes, symptoms and body weight of the patient but also depending upon the compound being administered.

"Tolerance" refers to a declining response to treatment over time.

"Drug tolerance" means a decreasing response to repeated constant doses of a drug or the need for increasing doses to maintain a constant response.

"Withdrawal" refers to a group of symptoms that occur upon the abrupt discontinuation or decrease in intake of medications or recreational drugs.

"Antinociceptive" refers to any factor that increases tolerance for, or reduces sensitivity to, a dangerous or harmful stimulus, i.e., a stimulus that causes pain.

"Dependence" refers to the need for one or more substances (i.e., drugs) to function. It is possible to be dependent on a drug and not be addicted. Dependence can be a bodily response to a substance. Dependence often occurs when a subject relies on medications to control a chronic medical condition.

D3R is dopamine 3 receptor agonist.

PRAM is pramipexole, a clinically available dopamine 3 receptor agonist with preference for dopamine 3 receptors.

Morph is morphine, which is an opioid prescribed for pain.

Oxycodone is a semi-synthetic opioid prescribed for pain.

"In combination with" means sufficiently close in time to produce a combined effect (that is, in combination with can be simultaneously, or it can be two or more events occurring within a short time period before or after each other). In some embodiments, the administration of two or more compounds in combination with means that the two compounds are administered closely enough in time that the presence of one alters the biological effects of the other. The two compounds can be administered in the same or different formulations or sequentially. Such concurrent administration can be carried out by mixing the compounds prior to administration, or by administering the compounds in two different formulations, for example, at the same point in time but at different anatomic sites or using different routes of administration.

"Chronic pain" is pain that extends beyond the expected period of healing, and may be considered pain that has lasted for at least three months.

A "subject" as used herein can be a human subject and can include, but is not limited to a patient. The subject may be male or female and may be of any race or ethnicity, including, but not limited to, Caucasian, African-American, African, Asian, Hispanic, Indian, etc. The subject may be of any age, including newborn, neonate, infant, child, juvenile, adolescent, adult, and geriatric. A subject can also include an animal subject, including mammalian subjects such as canines, felines, bovines, caprines, equines, ovines, porcines, rodents (e.g. rats and mice), lagomorphs, primates (including non-human primates), etc., for prevention and treatment purposes as well as veterinary medicine and/or pharmaceutical drug development purposes. A subject of this invention can be experiencing pain and/or are at increased risk of experiencing pain, e.g., as a result of surgery and/or a medical procedure.

Having now described the invention, the same will be illustrated with reference to certain examples, which are included herein for illustration purposes only, and which are not intended to be limiting of the invention.

EXAMPLES

Example 1. Maintaining Opioid Efficacy in the Treatment of Chronic Pain by Adjuvant Use of Dopamine Receptor Compounds In pilot studies, we found that loss of dopamine 3 receptor (D3R) function in D3 receptor knockout mice (D3KO) led to an opioid-tolerant phenotype, which mirrored the behavioral state observed in a rat model of chronic neuropathic pain. Importantly, in this chronic pain model, treatment with low-dose morphine became ineffective in modulating pain withdrawal responses. Adding a D3R agonist to the opioid treatment paradigm restored opioid efficacy in animals under chronic pain and was able to do so at reduced opioid doses, which on their own were not even effective in uninjured animals. In parallel studies, we found that a combination treatment of a D3R agonist with morphine prevented the development of morphine tolerance, while animals treated with morphine only became tolerant. Based on these preliminary studies, targeting the D3R system provides a novel tool by which to prevent or rescue the development of opioid induced tolerance in chronic pain patients, and this new treatment will extend the efficacy of the pain treatment well beyond the effective time frame of opioids currently used in the clinic.

Pain is the most common reason Americans access the health care system, and chronic pain affects more Americans that diabetes, heart disease and cancer combined. An estimated 100 million Americans suffer from chronic pain, which has an annual economic impact of >$600 billion.

Opioid analgesics are the most commonly prescribed class of medications in the US, and ~11.5 million patients are currently on a long-term opioid therapy. However, while opioids are very effective in controlling pain and other sensory disorders under acute conditions (such as after trauma or post-surgery), complications of long-term (chronic) use include loss of effect over time (tolerance), risk of addiction or dependence, misuse/abuse and accidental overdose.

This invention provides a new therapeutic approach for the treatment of chronic pain conditions using a novel and non-obvious combination of existing, FDA-approved drugs. In particular, this invention provides a novel combination of opioids and D3R agonists to treat pain, e.g., chronic pain, to maintain efficacy over time and reduce at the same time the dose of the opioids needed to prevent the development of addiction and accidental overdose.

In some embodiments, this invention targets subjects who have chronic pain conditions that require long-term or life-long treatment strategies.

This invention solves the well-established problem of opioid tolerance in the long-term treatment of chronic pain and reduces the risk of addiction. Adding a dopamine D3 receptor agonist to the opioid based treatment of chronic pain patients will restore 'normality' and a long-lasting pain free state in these patients, thus improving quality of life. The combination therapy can be used to restore opioid efficacy in patients that no longer respond to opioids, or in new patients to prevent opioid tolerance from developing while still maintaining the analgesic effect provided by the opioids. Activation of D3 receptor function will restore the pain relieving (analgesic) actions of the initial opioid-based therapy for patients in chronic pain.

Example 2. Dopamine Receptor Modulators Enhance Opioid Analgesia in a Rodent Model of Spinal Cord Injury Background: Opiate agonists such as morphine are often ineffective in neuropathic pain related to spinal cord injuries (SCI) and also carry a high risk for addiction and dependence. There is a need to identify other possible analgesic agents that are effective at managing chronic SCI-related pain, without the unwanted side effects of opiates.

Purpose: This study examined the pairing of low-dose morphine with dopamine D3 and D1 receptor modulators to improve analgesia for SCI-related pain, while reducing morphine's rewarding effects.

Methods: 55 female, Long-Evans rats were tested for mechanical thresholds prior to receiving a spinal contusion (SCI) or sham surgery. Mechanical pain thresholds were measured 21-27 days post-surgery under the following conditions: Morphine alone (1.0 or 2.5 mg/kg); Morphine (1.0 or 2.5 mg/kg)+0.1 mg/kg Pramipexole (PRAM; D3R agonist); Morphine (2.5 mg/kg)+0.1 mg/kg SCH23390 (SCH: D1R antagonist); 0.1 mg/kg Pramipexole alone; 0.1 mg/kg SCH23390 alone. Conditioned Place Preference (CPP) to each drug combination was assessed to determine the addictive potential of that specific combination.

Results: In sham animals, the addition of PRAM to 1.0 mg/kg of morphine increased mechanical thresholds over that of baseline and morphine alone. PRAM had no additional effect when added to 2.5 mg/kg morphine. Neither PRAM nor SCH alone provided analgesia in sham animals compared to baseline. In SCI animals, PRAM and SCH increased analgesia over morphine alone when combined with 2.5 mg/kg of morphine. Neither PRAM nor SCH exacerbated CPP to morphine at either dose in sham or SCI animals.

Conclusions: Pairing a dopamine D3 receptor agonist with low dose morphine provides better analgesia than morphine alone without exacerbating the addictive potential of morphine for SCI-related pain. This combination therapy may represent a potential clinical therapeutic intervention for neuropathic pain.

Example 3. Dopamine Receptor Modulators Enhance Opioid Analgesia in a Rodent Model of Spinal Cord Injury Introduction Of the estimated 23 million individuals worldwide with spinal cord injuries (SCI), one-third experience chronic neuropathic pain that can be refractory to commonly used analgesics. Neuropathic pain is often treated with opioids, but long term opioid use is problematic, resulting in tolerance and addiction. There is extensive overlap in the intracellular signaling pathways of dopamine (DA) and opioid receptors, and lack of a functioning dopamine 3 receptor (D3R) leads to a reduction in analgesic efficacy provided by opioids. The objective of this study is to demonstrate in vivo that a combination of opioids and D3R agonists provides superior analgesia for neuropathic pain associated with SCI, but does not exacerbate the motivational effects seen with morphine alone. This is based on the hypothesis that a combination of morphine and the D3 receptor agonist pramipexole will provide better pain relief after SCI than morphine alone Methods Mechanical thresholds were assessed in 3-5 month old female Long-Evans rats before and ~21 days after a mild, traumatic SCI (contusion model). Thresholds were re-assessed after i.p. injection of: Morphine 1.0 mg/kg with and without 0.1 mg/kg pramipexole (PRAM) or Morphine 2.5 mg/kg with and without 0.1 mg/kg PRAM. Conditioned place preference was performed under each drug condition (5 days alternating drug/vehicle pairing, with testing on day 6). Western blotting determined expression of D3R, D1R and u-opioid receptor (MOR) in the lumbar spinal cord.

CONCLUSIONS

Mild, traumatic SCI results in significantly reduced mechanical thresholds compared to baseline. Following SCI, adding a D3 receptor agonist to 2 different doses of morphine raised mechanical thresholds to a level significantly above baseline and significantly improved analgesia compared to either dose of morphine alone. Preference towards drug treatment was induced only when using the higher dose of morphine in combination with pramipexole. SCI led to increased expression of D1R and increased phosphorylation of the MOR. These data suggest that adjuvant activation of the D3R in conjunction with morphine allows morphine to provide analgesia at doses that do not invoke the reward pathway. Future studies will determine if this combination therapy prevents or inhibits the emergence of tolerance in the treatment of chronic pain conditions.

The foregoing is illustrative of the present invention, and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

That which is claimed:

1. A method of treating pain in a subject in need thereof, comprising administering to the subject an effective amount of an opioid and a dopamine type 3 receptor (D3R) agonist, wherein the D3R agonist allows for a lower dose of the opioid to be administered to achieve pain relief as compared to administration of the lower dose of the opioid without the D3R agonist thereby treating pain in the subject, wherein the opioid is a mu-opioid receptor (MOR) agonist.

2. The method of claim 1, wherein the pain is chronic pain.

3. The method of claim 1, wherein the pain is acute pain.

4. A method of reducing or inhibiting opioid tolerance in a subject in need thereof, comprising administering to the subject an effective amount of an opioid and a dopamine type 3 receptor (D3R) agonist, wherein the D3R agonist allows for a lower dose of the opioid to be administered to achieve reduction or inhibition of opioid tolerance as compared to administration of the lower dose of the opioid without the D3R agonist thereby reducing or inhibiting opioid tolerance in the subject, wherein the opioid is a mu-opioid receptor (MOR) agonist.

5. A method of restoring opioid efficacy in a subject in need thereof, comprising administering to the subject an effective amount of an opioid and a dopamine type 3 receptor (D3R) agonist, wherein the D3R agonist allows for a lower dose of the opioid to be administered to achieve restoration of opioid efficacy as compared to administration of the lower dose of the opioid without the D3R agonist thereby restoring opioid efficacy in the subject, wherein the opioid is a mu-opioid receptor (MOR) agonist.

6. The method of claim 1, wherein the D3R agonist and the opioid are administered in the same composition.

7. The method of claim 1, wherein the D3R agonist and the opioid are administered in separate compositions.

8. The method of claim 7, wherein the D3R agonist and the opioid are administered by the same route.

9. The method of claim 7, wherein the D3R agonist and the opioid are administered by different routes.

10. The method of claim 1, wherein the D3R agonist and the opioid are administered via one or more of oral administration, injection, patch, and a surgically implanted pump.

11. The method of claim 1, further comprising delivering to the subject an additional therapeutic agent.

12. The method of claim 11, wherein the additional therapeutic agent is an analgesic.

13. The method of claim 1, wherein the subject is a human.

* * * * *

UNITED STATES PATENT AND TRADEMARK OFFICE
CERTIFICATE OF CORRECTION

| | | |
|---|---|---|
| PATENT NO. | : 12,383,551 B2 | Page 1 of 1 |
| APPLICATION NO. | : 18/443447 | |
| DATED | : August 12, 2025 | |
| INVENTOR(S) | : Kori Brewer and Stefan Clemens | |

It is certified that error appears in the above-identified patent and that said Letters Patent is hereby corrected as shown below:

On the Title Page

Item (74) Change "Stanek Lemon Crouse & Lemon" to -- Stanek Lemon Crouse & Meeks --

Signed and Sealed this
Sixteenth Day of September, 2025

Coke Morgan Stewart
*Acting Director of the United States Patent and Trademark Office*